US009266880B2

(12) United States Patent
Austin et al.

(10) Patent No.: US 9,266,880 B2
(45) Date of Patent: Feb. 23, 2016

(54) SUBSTITUTED AZAINDAZOLE COMPOUNDS

(75) Inventors: Joel F. Austin, Secaucus, NJ (US); David B. Frennesson, Naugatuck, CT (US); Mark G. Saulnier, Higganum, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 273 days.

(21) Appl. No.: 13/884,676

(22) PCT Filed: Nov. 9, 2011

(86) PCT No.: PCT/US2011/059914
§ 371 (c)(1),
(2), (4) Date: May 10, 2013

(87) PCT Pub. No.: WO2012/064815
PCT Pub. Date: May 18, 2012

(65) Prior Publication Data
US 2013/0231354 A1  Sep. 5, 2013

Related U.S. Application Data

(60) Provisional application No. 61/412,995, filed on Nov. 12, 2010.

(51) Int. Cl.
*C07D 487/04*  (2006.01)
*C07D 471/04*  (2006.01)

(52) U.S. Cl.
CPC ............ *C07D 471/04* (2013.01); *C07D 487/04* (2013.01)

(58) Field of Classification Search
CPC ................ C07D 487/04; C07D 471/04
See application file for complete search history.

(56) References Cited

U.S. PATENT DOCUMENTS

| | | | |
|---|---|---|---|
| 6,124,463 A | 9/2000 | Beck et al. | |
| 6,362,180 B1 | 3/2002 | Wilde et al. | |
| 8,779,142 B2 * | 7/2014 | Kitade et al. | 546/118 |
| 2008/0039491 A1 | 2/2008 | Ronan et al. | |
| 2008/0255085 A1 | 10/2008 | Arvidsson et al. | |
| 2012/0108589 A1 | 5/2012 | Kitade et al. | |
| 2013/0045980 A1 | 2/2013 | Velaparthi et al. | |
| 2013/0184254 A1 | 7/2013 | Velaparthi et al. | |

FOREIGN PATENT DOCUMENTS

| | | |
|---|---|---|
| WO | WO98/08847 | 3/1998 |
| WO | WO00/01675 | 1/2000 |
| WO | WO03/027094 | 4/2003 |
| WO | WO2005/051906 | 6/2005 |
| WO | WO2006/004188 | 1/2006 |
| WO | WO2007/038314 | 4/2007 |
| WO | WO2008/030579 | 3/2008 |
| WO | WO2008/070354 | 6/2008 |
| WO | WO2008/075109 | 6/2008 |
| WO | WO2009/017954 | 2/2009 |
| WO | WO2010/059788 | 5/2010 |
| WO | WO2010/129668 | 11/2010 |
| WO | WO2012/015723 | 2/2012 |
| WO | WO2012/044537 | 4/2012 |
| WO | WO2012/064815 | 5/2012 |
| WO | WO2013/049263 | 4/2013 |

OTHER PUBLICATIONS

Diaz-Ortiz, "First Diels-Alder Reaction of Pyrazolyl Imines under Microwave Irradiation", Synlett 1998; 1998(10): 1069-1070.*
Diaz-Ortiz, A., et al., "Synthesis of Pyrazolo[3,4-b]pyridines by Cycloaddition Reactions Under Microwave Irradiation," Tetrahedron, vol. 56, pp. 1569-1577 (2000).
Chinese Search Report issued Sep. 18, 2014.
Moreira, V.M.A., et al., "Synthesis and evaluation of novel 17-indazole androstene derivatives designed as CYP17 inhibitors," Steroids 72 (2007), pp. 939-948.
International Preliminary Report on Patentability for PCT/US2011/059914.

* cited by examiner

*Primary Examiner* — Sreeni Padmanabhan
*Assistant Examiner* — Sahar Javanmard
(74) *Attorney, Agent, or Firm* — Gary D. Greenblatt

(57) ABSTRACT

Disclosed are azaindazole compounds of Formula (I): or pharmaceutically acceptable salts thereof, wherein: Q is: (i) 5-membered heteroaryl comprising at least one nitrogen heteroatom and substituted with zero to 2 Rg; or (ii) 9- to 10-membered bicyclic heteroaryl selected from Formula (II) and; wherein Ring A is a 5- to 6-membered aryl or heteroaryl fused ring substituted with zero to 2 Rg; and R1, R2, R3, and Rg are defined herein. Also disclosed are methods of using such compounds in the treatment of at least one CYP17 associated condition, such as, for example, cancer, and pharmaceutical compositions comprising such compounds.

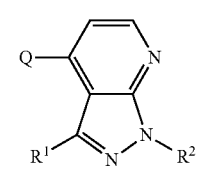

(I)

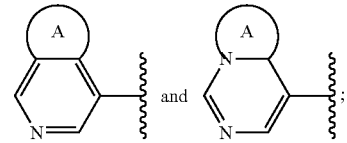

(II)

13 Claims, No Drawings

SUBSTITUTED AZAINDAZOLE COMPOUNDS

FIELD OF THE INVENTION

The present invention generally relates to substituted azaindazole compounds useful as CYP17 inhibitors. Provided herein are substituted azaindazole compounds, compositions comprising such compounds, and methods of their use. The invention further pertains to pharmaceutical compositions comprising at least one compound according to the invention that is useful for the treatment of conditions related to the CYP17 enzyme, such as cancer and other proliferative diseases.

BACKGROUND OF THE INVENTION

Prostate cancer is the second leading cause of cancer related mortality in American men. In 2007, there were 218,890 new cases with 27,000 deaths associated with prostate cancer. It is well known that androgens, such as testosterone and dihydrotestosterone, drive the growth of the prostate as well as prostate cancer at the level of the androgen receptor. The standard of care for advanced hormone sensitive prostate cancer involves surgical or chemical castration with a leutenizing releasing hormone agonist/antagonist to remove the androgens produced in the gonads from circulation. However, approximately 90% of androgens are produced in the testes with the remaining 10% being produced through the action of the adrenal gland. Thus, castration does not alleviate the action of all androgens. Further once a patient progresses to castration resistant prostate cancer, androgens are also produced at the level of the tumor, making treatment with anti-androgens more difficult.

The cytochrome P450 CYP17 is responsible for the biosynthesis of both dihydroepiandrostenedione and androstenedione which are precursors of both androgens and estrogen. Thus the production of all androgens and estrogens produced in the human body is mediated by CYP17. Blocking this enzyme would inhibit the production of gonadal, adrenal and tumoral androgens and could offer a new treatment option for prostate cancer and estrogen receptor-positive breast cancer patients.

Clinical proof-of-concept for CYP17 as a target for prostate cancer has been achieved with the antifungal ketoconazole and the steroidal CYP17 inhibitor abiraterone, which has progressed to Phase III clinical trials for prostate cancer.

There remains a need for compounds that are useful as inhibitors of CYP17 enzymes.

Applicants have found potent compounds that have activity as CYP17 inhibitors. These compounds are provided to be useful as pharmaceuticals with desired stability, bioavailability, therapeutic index, and toxicity values that are important to their drugability.

BRIEF STATEMENT OF THE INVENTION

The present invention fills the foregoing need by providing substituted azaindazole compounds, which are useful as inhibitors of CYP17 enzymes, including salts and prodrugs thereof.

The present invention also provides pharmaceutical compositions comprising a pharmaceutically acceptable carrier; and at least one compound of Formula (I), or salts or prodrugs thereof.

The present invention also provides a method of treating a disease or disorder associated with the activity of the CYP17 enzyme, the method comprising administering to a mammalian patient a compound of Formula (I) or pharmaceutically acceptable salts or prodrugs thereof.

The present invention also provides processes and intermediates for making the compounds of Formula (I) or salts or prodrugs thereof.

The present invention also provides the compounds of Formula (I), or pharmaceutically acceptable salts or prodrugs thereof, for use in therapy.

The present invention also provides use of a compound of Formula (I) or pharmaceutically acceptable salts or prodrugs thereof, for the manufacture of a medicament for the treatment of cancer.

The compounds of Formula (I) and compositions comprising the compounds are inhibitors of CYP17 enzymes, and may be used in treating, prevention, or curing various CYP17 enzyme related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

DETAILED DESCRIPTION OF THE INVENTION

The first aspect of the invention provides compounds of Formula (I):

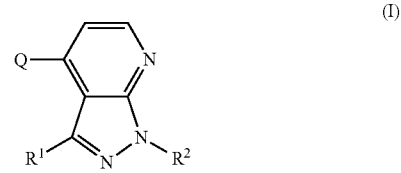

or pharmaceutically acceptable salts or prodrugs thereof, wherein:
Q is:
  (i) a 5-membered heteroaryl comprising at least one nitrogen heteroatom and substituted with zero to 2 $R^g$; or
  (ii) a 9- to 10-membered bicyclic heteroaryl selected from

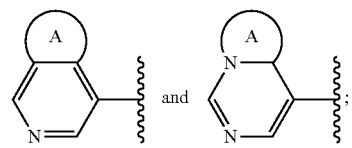

wherein Ring A is a 5- to 6-membered aryl or heteroaryl fused ring substituted with zero to 2 $R^g$;
$R^1$ is:
  (i) H, halo, —CN, —$OR^d$, —$NR^eR^e$, or —$C(O)OR^f$;
  (ii) $C_{1-6}$alkyl substituted with zero to 4 $R^a$;
  (iii) $C_{3-6}$ cycloalkyl substituted with zero to 4 $R^a$;
  (iv) aryl substituted with zero to 6 $R^b$;
  (v) heterocyclyl substituted with zero to 6 $R^c$; or
  (vi) heteroaryl substituted with zero to 6 $R^c$;
$R^2$ is:
  (i) $C_{1-6}$alkyl substituted with zero to 4 $R^a$;
  (ii) $C_{3-6}$ cycloalkyl substituted with zero to 4 $R^a$;
  (iii) —$S(O)_2(C_{1-4}alkyl)$, —$S(O)_2(C_{1-4}fluoroalkyl)$, or —$C(O)(C_{1-6}alkyl)$;
  (iv) aryl substituted with zero to 6 $R^b$;

(v) heterocyclyl substituted with zero to 6 $R^c$; or (vi) heteroaryl substituted with zero to 6 $R^c$;

each $R^a$ is independently halo, —OH, —CN, $C_{3-6}$cycloalkyl, $C_{1-2}$fluoroalkyl, $C_{1-6}$alkoxy, $C_{1-2}$fluoroalkoxy, —$NR^fR^f$, phenyl substituted with zero to 5 $R^b$, phenoxy substituted with zero to 4 $R^b$, heterocyclyl substituted with zero to 4 $R^c$, and/or heteroaryl substituted with zero to 4 $R^b$;

each $R^b$ is independently halo, —OH, —CN, $C_{1-4}$alkyl, $C_{3-6}$cycloalkyl, $C_{1-2}$fluoroalkyl, $C_{1-6}$alkoxy, $C_{1-4}$fluoroalkoxy, —$NR^fR^f$, —C(O)OH, —S(O)$_2$(C$_{1-4}$alkyl), —S(O)$_2$ $NR^fR^f$, and/or heterocyclyl substituted with zero to 4 $R^c$;

each $R^c$ is independently halo, —CN, —OH, $C_{1-4}$alkyl, $C_{3-6}$cycloalkyl, $C_{1-2}$fluoroalkyl, $C_{1-6}$alkoxy, $C_{1-4}$fluoroalkoxy, —$NR^fR^f$, azetidine, and/or pyrrolidine, or two $R^c$ attached to the same atom can form =O;

each $R^d$ is:

(i) $C_{1-4}$alkyl substituted with zero to 4 $R^a$;

(ii) $C_{3-6}$ cycloalkyl substituted with zero to 4 $R^a$;

(iii) aryl substituted with zero to 6 $R^b$;

(iv) heterocyclyl substituted with zero to 6 $R^c$; and/or (v) heteroaryl substituted with zero to 6 $R^c$;

each $R^e$ is independently:

(i) H;

(ii) $C_{1-4}$alkyl substituted with zero to 4 $R^a$; and/or (iii) $C_{3-6}$ cycloalkyl substituted with zero to 4 $R^a$;

or two $R^e$ attached to the same nitrogen atom can form a 5-6 membered heterocyclyl ring having one additional heteroatom, and substituted with zero to 2 substituents independently selected from —CN, —OH, and/or $C_{1-4}$alkyl:

each $R^f$ is independently H, $C_{1-6}$alkyl, $C_{3-6}$cycloalkyl, $C_{1-4}$fluoroalkyl, and/or aryl; and each $R^g$ is independently:

(i) halo, —CN, —$OR^d$, —$NR^eR^e$, or —C(O)$OR^f$;

(ii) $C_{1-6}$alkyl substituted with zero to 4 $R^a$;

(iii) $C_{3-6}$ cycloalkyl substituted with zero to 4 $R^a$;

(iv) aryl substituted with zero to 6 $R^b$;

(v) heterocyclyl substituted with zero to 6 $R^c$; or (vi) heteroaryl substituted with zero to 6 $R^c$.

One embodiment provides a compound of Formula (I) or a pharmaceutically acceptable salt or a prodrug thereof, wherein Q is a 5-membered heteroaryl comprising at least one nitrogen heteroatom and substituted with zero to 2 $R^g$. Included in this embodiment are compounds in which Q is pyrrolyl, pyrazolyl, imidazolyl, isoxazolyl, oxazolyl, isothiazolyl, thiazolyl, triazolyl, and oxadiazolyl.

One embodiment provides a compound of Formula (I) or a pharmaceutically acceptable salt or a prodrug thereof, wherein Q is an imidazolyl substituted with zero to 2 $R^g$. Included in this embodiment are compounds in which Q is:

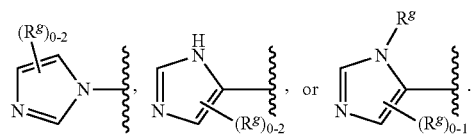

One embodiment provides a compound of Formula (I) or a pharmaceutically acceptable salt or a prodrug thereof, wherein Q is a 9- to 10-membered bicyclic heteroaryl selected from:

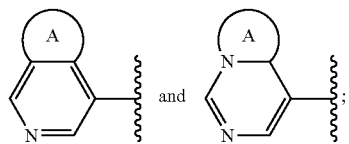

wherein Ring A is a 5- to 6-membered aryl or heteroaryl fused ring substituted with zero to 2 $R^g$. Examples of suitable 9- to 10-membered bicyclic heteroaryl groups include pyrrolo[1,2-c]pyrimidinyl, isoquinolinyl, 4aH-pyrido[1,2-c]pyrimidinyl, 1,6-naphthyridinyl, and 1,7-naphthyridinyl.

One embodiment provides a compound of Formula (I) or a pharmaceutically acceptable salt or a prodrug thereof, wherein Q is:

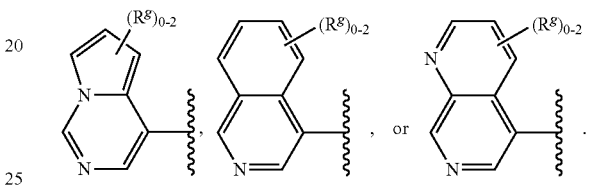

One embodiment provides a compound of Formula (I) or a pharmaceutically acceptable salt or a prodrug thereof, wherein $R^1$ is H, halo, —CN, —$OR^d$, —$NR^eR^e$, or —C(O)$OR^f$, and $R^d$, $R^e$, and $R^f$ are defined in the first aspect hereinabove. Included in this embodiment are compounds in which $R^1$ is H, F, Cl, —CN, —OH, —OCH$_3$, —NH$_2$, —NHCH$_3$, —N(CH$_3$)$_2$, —COOH, or —COOCH$_3$.

One embodiment provides a compound of Formula (I) or a pharmaceutically acceptable salt or a prodrug thereof, wherein $R^1$ is $C_{1-6}$alkyl substituted with zero to 4 $R^a$. Included in this embodiment are compounds in which $R^1$ is $C_{1-4}$alkyl substituted with zero to 4 $R^a$. Suitable $R^1$ include, for example, —CH$_3$, —CH$_2$CH$_3$, —CH$_2$F, —CF$_3$, —CH$_2$OH, —CH$_2$NH$_2$, —CH$_2$CN, and —CH$_2$(C$_{3-6}$cycloalkyl).

One embodiment provides a compound of Formula (I) or a pharmaceutically acceptable salt or a prodrug thereof, wherein $R^1$ is $C_{3-6}$ cycloalkyl substituted with zero to 4 $R^a$.

One embodiment provides a compound of Formula (I) or a pharmaceutically acceptable salt or a prodrug thereof, wherein $R^1$ is aryl substituted with zero to 6 $R^b$ Included in this embodiment are compounds in which $R^1$ is phenyl substituted with zero to 3 $R^b$. Suitable $R^1$ groups include, for example, phenyl substituted with zero to 3 $R^b$ independently selected from F, Cl, —CN, —OH, —CH$_3$, —CF$_3$—OCH$_3$, —OCF$_3$, —NH$_2$, and/or —SO$_2$NH$_2$.

One embodiment provides a compound of Formula (I) or a pharmaceutically acceptable salt or a prodrug thereof, wherein $R^1$ is heterocyclyl substituted with zero to 6 $R^c$. Included in this embodiment are compounds in which $R^1$ is azetidinyl, tetrahydrofuranyl, pyrrolidinyl, tetrahydropyranyl, piperidinyl, morpholinyl, or piperazinyl substituted with zero to 4 $R^c$.

One embodiment provides a compound of Formula (I) or a pharmaceutically acceptable salt or a prodrug thereof, wherein $R^1$ is heteroaryl substituted with zero to 6 $R^c$. Included in this embodiment are compounds in which $R^1$ is pyrrolyl, furanyl, pyrazolyl, imidazolyl, isoxazolyl, oxazolyl, thiazolyl, triazolyl, oxadiazolyl, pyridinyl, pyridazinyl, pyrimidinyl, or pyrazinyl substituted with zero to 3 $R^c$.

One embodiment provides a compound of Formula (I) or a pharmaceutically acceptable salt or a prodrug thereof, wherein $R^2$ is $C_{1-6}$alkyl substituted with zero to 4 $R^a$. Included in this embodiment are compounds in which $R^2$ is $C_{1-4}$alkyl substituted with zero to 4 $R^a$.

One embodiment provides a compound of Formula (I) or a pharmaceutically acceptable salt or a prodrug thereof, wherein $R^2$ is $C_{3-6}$ cycloalkyl substituted with zero to 4 $R^a$.

One embodiment provides a compound of Formula (I) or a pharmaceutically acceptable salt or a prodrug thereof, wherein $R^2$ is —S(O)$_2$(C$_{1-4}$alkyl), —S(O)$_2$(C$_{1-4}$fluoroalkyl), or —C(O)(C$_{1-6}$alkyl). Included in this embodiment are compounds in which $R^2$ is —S(O)$_2$(C$_{1-2}$alkyl), —S(O)$_2$(C$_{1-2}$fluoroalkyl), or —C(O)(C$_{1-3}$alkyl).

One embodiment provides a compound of Formula (I) or a pharmaceutically acceptable salt or a prodrug thereof, wherein $R^2$ is aryl substituted with zero to 6 $R^b$. Included in this embodiment are compounds in which $R^2$ is phenyl substituted with zero to 4 $R^b$. Suitable $R^2$ groups include, for example, phenyl substituted with zero to 4 $R^b$ independently selected from F, Cl, —CN, —OH, —CH$_3$, —CF$_3$ —OCH$_3$, —OCF$_3$, —NH$_2$, and/or —SO$_2$NH$_2$.

One embodiment provides a compound of Formula (I) or a pharmaceutically acceptable salt or a prodrug thereof, wherein $R^2$ is heterocyclyl substituted with zero to 6 $R^c$. Included in this embodiment are compounds in which $R^2$ is azetidinyl, tetrahydrofuranyl, pyrrolidinyl, tetrahydropyranyl, piperidinyl, morpholinyl, or piperazinyl substituted with zero to 4 $R^c$.

One embodiment provides a compound of Formula (I) or a pharmaceutically acceptable salt or a prodrug thereof, wherein $R^2$ is heteroaryl substituted with zero to 6 $R^c$. Included in this embodiment are compounds in which $R^2$ is pyrrolyl, furanyl, pyrazolyl, imidazolyl, isoxazolyl, oxazolyl, thiazolyl, triazolyl, oxadiazolyl, pyridinyl, pyridazinyl, pyrimidinyl, or pyrazinyl substituted with zero to 3 $R^c$.

One embodiment provides a compound of Formula (I) or a pharmaceutically acceptable salt or a prodrug thereof, wherein:
Q is:

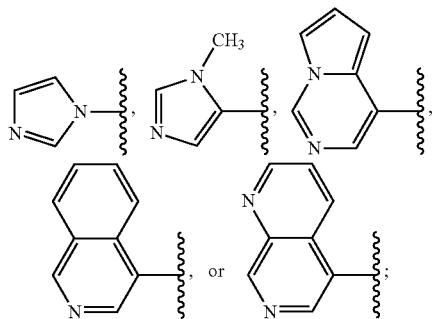

$R^1$ is H;
$R^2$ is fluorophenyl, difluorophenyl, or phenyl substituted with —SO$_2$NH$_2$.

One embodiment provides a compound of Formula (I) or a pharmaceutically acceptable salt or a prodrug thereof, wherein said compounds is selected from 4-(1-(4-fluorophenyl)-1H-pyrazolo[3,4-b]pyridin-4-yl)isoquinoline (1); 1-(4-fluorophenyl)-4-(1H-imidazol-1-yl)-1H-pyrazolo[3,4-b]pyridine (2); 5-(1-(4-fluorophenyl)-1H-pyrazolo[3,4-b]pyridin-4-yl)-1,7-naphthyridine (3); 1-(4-fluorophenyl)-4-(1-methyl-1H-imidazol-5-yl)-1H-pyrazolo[3,4-b]pyridine (4); 3-(4-(1,7-naphthyridin-5-yl)-1H-pyrazolo[3,4-b]pyridin-1-yl)benzenesulfonamide (5); 3-(4-(1-methyl-1H-imidazol-5-yl)-1H-pyrazolo[3,4-b]pyridin-1-yl)benzenesulfonamide (6); 3-(4-(isoquinolin-4-yl)-1H-pyrazolo[3,4-b]pyridin-1-yl)benzenesulfonamide (7); and 1-(2,4-difluorophenyl)-4-(pyrrolo[1,2-c]pyrimidin-4-yl)-1H-pyrazolo[3,4-b]pyridine (8).

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "C$_{1-6}$alkyl" denotes straight and branched chain alkyl groups with one to six carbon atoms.

The term "haloalkyl," as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl (—CH$_2$Cl), trifluoromethyl (—CF$_3$—, and 2,2,2-trifluoroethyl (—CH$_2$CF$_3$). When numbers appear in a subscript after the symbol "C", the subscript defines with more specificity the number of carbon atoms that a particular haloalkyl group may contain. For example, "C$_{1-4}$haloalkyl" denotes straight and branched chain haloalkyl groups with one to four carbon atoms.

The term "fluoroalkyl" as used herein is intended to include both branched and straight-chain saturated aliphatic hydrocarbon groups substituted with one or more fluorine atoms. For example, "C$_{1-4}$ fluoroalkyl" is intended to include C$_1$, C$_2$, C$_3$, and C$_4$ alkyl groups substituted with one or more fluorine atoms. Representative examples of fluoroalkyl groups include, but are not limited to, —CF$_3$ and —CH$_2$CF$_3$.

The term "cyano" refers to the group —CN.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "C$_{3-6}$cycloalkyl" denotes cycloalkyl groups with three to six carbon atoms.

The term "alkoxy," as used herein, refers to an alkyl group attached to the parent molecular moiety through an oxygen atom, for example, methoxy group (—OCH$_3$).

"Fluoroalkoxy" and "—O(fluoroalkyl)" represent a fluoroalkyl group as defined above attached through an oxygen linkage (—O—). For example, "C$_{1-4}$fluoroalkoxy" is intended to include C$_1$, C$_2$, C$_3$, and C$_4$ fluoroalkoxy groups.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl.

The term "phenoxy," as used herein, refers to a phenyl group attached to the parent molecular moiety through an oxygen atom.

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or nonaromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazolyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th Edition, p. 1418, Mack Publishing Company, Easton, Pa. (1985), the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Any compound that can be converted in vivo to provide the bioactive agent (i.e., the compound of Formula (I)) is a prodrug within the scope and spirit of the invention.

The term "prodrugs" as employed herein includes amides and carbamates formed by reacting one or more amino groups of compounds of Formula (I) with alkyl, alkoxy, or aryl substituted acylating agents employing procedures known to those skilled in the art to generate amides, ureas, carbamates, and the like.

Various forms of prodrugs are well known in the art and are described in:

a) Wermuth, C. G. et al., *The Practice of Medicinal Chemistry*, Ch. 31, Academic Press (1996);

b) Bundgaard, H., ed., *Design of Prodrugs*, Elsevier, (1985);

c) Krogsgaard-Larson, P. et al., eds. *A Textbook of Drug Design and Development*, Ch. 5, pp. 113-191, Harwood Academic Publishers (1991); and d) Testa, B. et al., *Hydrolysis in Drug and Prodrug Metabolism*, Wiley-VCH (2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an antagonist of CYP17 enzyme, or effective to treat cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention are intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 0.5 to 2000 mg, preferably from about 0.5 to 500 mg, more preferably from about 0.5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 100 mg/kg body weight, preferably between about 0.05 and about 50 mg/kg body weight and most preferably between about 0.05 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl alcohol, and/or polyvinylpyrrolidone, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

Utility

The compounds of Formula (I) are useful for the treatment of cancer, for example, cancers dependent upon androgen receptor signaling. These compounds inhibit the activity of the CYP17 enzyme, which is involved in biosynthesis of androgens and estrogens. Blocking this enzyme would inhibit the production of gonadal, adrenal, and tumoral androgens and offers a new treatment option for cancers dependent upon androgen receptor and estrogen receptor signaling, such as prostate cancer and estrogen receptor-positive breast cancer patients. Thus, the treatment comprises administering to the patient a compound of Formula (I) or a pharmaceutically acceptable salt or prodrug thereof.

In one embodiment, a method is provided for treating cancer comprising administering compound of Formula (I) or a pharmaceutically acceptable salt or prodrug thereof to a mammal in need thereof. The method of this embodiment can be used to treat a variety of cancers, including, but not limited to, breast cancer, ovarian cancer, and prostate cancer. Preferably, the method of this embodiment is used to treat prostate cancer or breast cancer. In one method of this embodiment, compound of Formula (I) is administered in a therapeutically effective amount.

In one embodiment, provided are methods for treating cancer in a patient wherein the cancer is dependent upon CYP17 activation, comprising administering to the patient in need thereof a compound of Formula (I) or a pharmaceutically acceptable salt or prodrug thereof. In one method of this embodiment, a compound of Formula (I) is administered to treat prostate cancer. In another method of this embodiment, a compound of Formula (I) is administered to treat breast cancer. Preferably, a therapeutically effective amount of Compound (I) is administered.

The amount of a compound of Formula (I) which is administered and the dosage regimen for treating a particular cancer depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.05 and about 50 mg/kg body weight and most preferably between about 0.05 to 20 mg/kg body weight, may be appropriate may be appropriate. The daily dose can be administered in one to four doses per day.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, a compound of Formula (I) may be administered in combination with other anti-cancer treatments useful in the treatment of cancer or other proliferative diseases. The invention herein further comprises use of a compound of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of a compound of Formula (I) and one or more additional agents in kit form, e.g., where they are packaged together or placed in separate packages to be sold together as a kit, or where they are packaged to be formulated together.

The compound of Formula (I) can be formulated or co-administered with other therapeutic agents that are selected for their particular usefulness in addressing side effects associated with the aforementioned conditions. For example, the compound of Formula (I) may be formulated with agents to prevent nausea, hypersensitivity and gastric irritation, such as antiemetics, and $H_1$ and $H_2$ antihistaminics.

The phrase "anti-cancer treatment" includes but is not limited to, for example, radiation therapy and surgery.

The other anti-cancer agents may be selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

The above other therapeutic agents, when employed in combination with a compound of Formula (I), can be used, for example, in those amounts indicated in the Physicians' Desk Reference (PDR) or as otherwise determined by one of ordinary skill in the art.

In one embodiment, a method is provided for treating cancer comprising administering to a mammal in need thereof a compound of Formula (I) or a pharmaceutically acceptable salt or prodrug thereof; administering a glucocorticoid; and optionally, one or more additional anticancer agent. Examples of suitable glucocorticoids include, but are not limited to, dexamethasone and prednisolone.

In one embodiment, a method is provided for treating cancer comprising administering to a mammal in need thereof a compound of Formula (I) or a pharmaceutically acceptable salt or prodrug thereof; administering a mineralocorticoid receptor antagonist; and optionally, one or more additional anticancer agent. Examples of suitable mineralocorticoid receptor antagonists include, but are not limited to, eplerenone.

In another embodiment, a compound of Formula (I) or a pharmaceutically acceptable salt thereof is used to treat prostate cancer.

In one embodiment, the patient is an animal.

In another embodiment, the patient is a mammalian species including, but not limited to, for example, humans and domestic animals, such as, for example, dogs, cats, and horses.

In one embodiment, the present invention provides a compound of Formula (I) or a pharmaceutically acceptable salt thereof for use in therapy.

In one embodiment, the use of a compound of Formula (I) or a pharmaceutically acceptable salt thereof in the manufacture of a medicament for the treatment of cancer, including prostate cancer, is provided.

In one embodiment, the use of a compound of Formula (I) or a pharmaceutically acceptable salt thereof in the manufacture of a medicament for the treatment of cancer, including breast cancer, is provided.

Methods of Preparation

The compounds of the present invention may be prepared by synthetic routes that include processes analogous to those well-known in the chemical arts, particularly in light of the description provided herein. For illustrative purposes, general Schemes 1-8 below show general methods for preparing the compounds of the present invention, as well as key intermediates. For a more detailed description of the individual reaction steps, see the Example section below. Those skilled in the art will appreciate that other synthetic routes may be used to synthesize the inventive compounds. Although specific starting materials and reagents are depicted in the Schemes and discussed below, other starting materials and reagents can easily be substituted to provide a variety of compounds of the present invention. In addition, many of the compounds prepared by the methods below can be further modified in light of this disclosure using conventional chemistry well known to those skilled in the art.

As shown in Scheme 1, for instance, the commercially available halogenated pyridine II can be condensed with various hydrazines of general formula III resulting in the formation of the intermediate hydrazone of general formula IV. Cyclization of the hydrazone can be promoted by heating to afford the 4-iodo-indazole of general structure V. Treatment of the iodide V with a Pd(II) species such as $PdCl_2(dppf)$ in the presence of a diboronic ester, such as bis-(pinacolato)diboron, and an inorganic base such as potassium acetate, will afford the boronic ester of general structure VI. The boronic ester VI can be coupled to heteroaromatic halides of general structure VII under standard Suzuki coupling conditions to afford compounds of general structure (I).

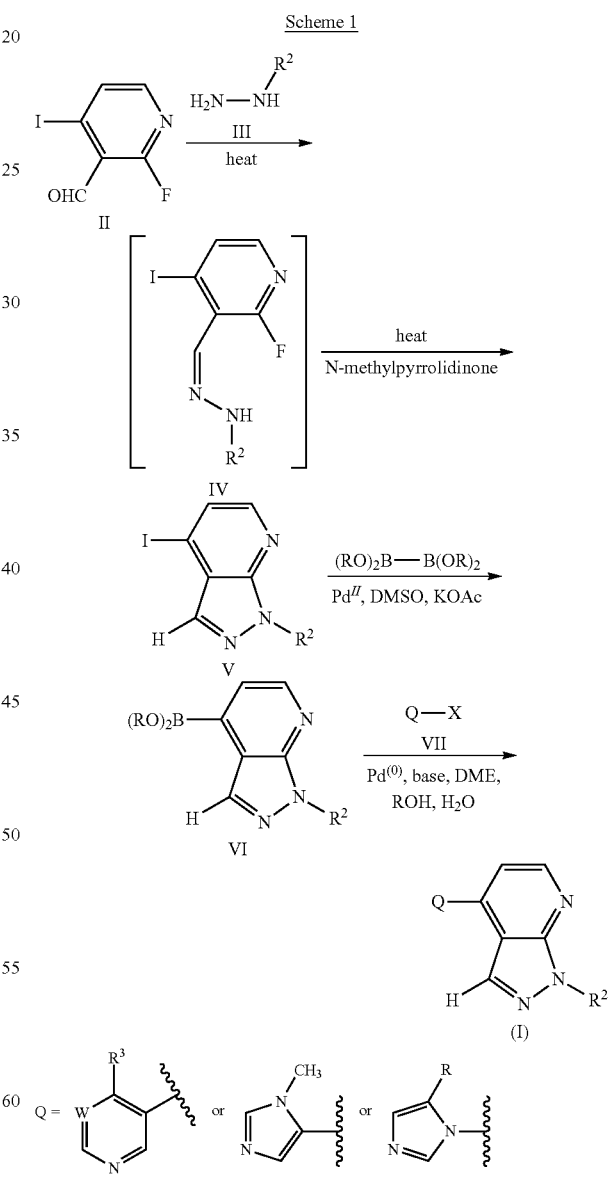

Alternatively, the aldehyde II can be treated with an alkyl or aryl lithium or Grignard reagent to afford the resulting benzylic alcohol which can subsequently be oxidized, by Dess-Martin periodinane for example, to afford the ketone of general structure VIII (Scheme 2). Treatment of the ketone with alkyl or aryl hydrazines III, will afford the intermediate hydrazone IX, which can cyclize to the indazole of general structure X. Treatment of the iodide X with a Pd(II) species such as PdCl$_2$(dppf) in the presence of a diboronic ester, such as bis-(pinacolato)diboron, and an inorganic base such as potassium acetate, will afford the boronic ester of general structure XI. The boronic ester VI can be coupled to heteroaromatic halides of general structure VII under standard Suzuki coupling conditions as depicted in Scheme 1 to make compounds of general structure (I).

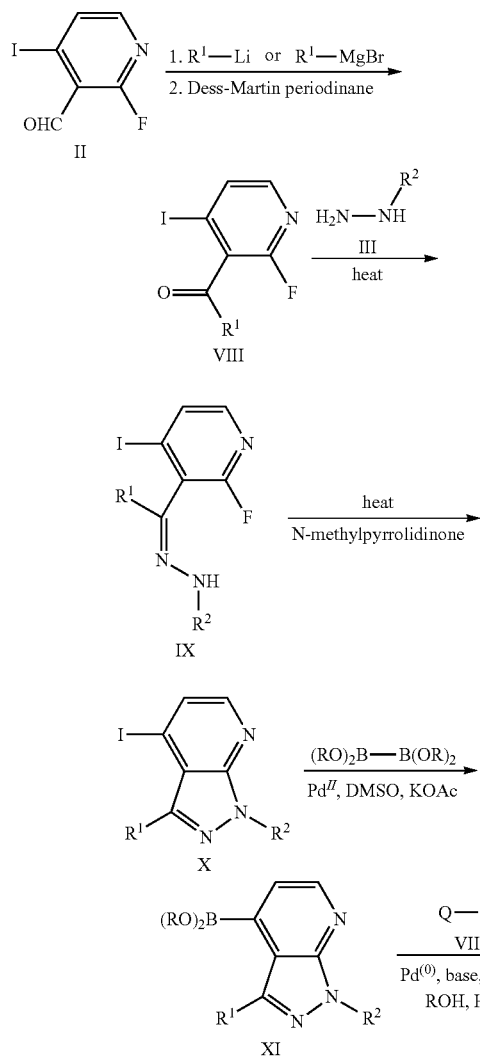

Additionally, halogenated heteroaromatics of general structure VII, can be treated with a Pd(II) species, such as PdCl$_2$(dppf) in the presence of a diboronic ester, such as bis-(pinacolato)diboron, and an inorganic base such as potassium acetate to afford the boronic ester of general structure XII (Scheme 3). The boronic ester can then be coupled to the aryl halide or triflate of general structure XIII under standard Suzuki coupling conditions to afford compounds of general structure (I).

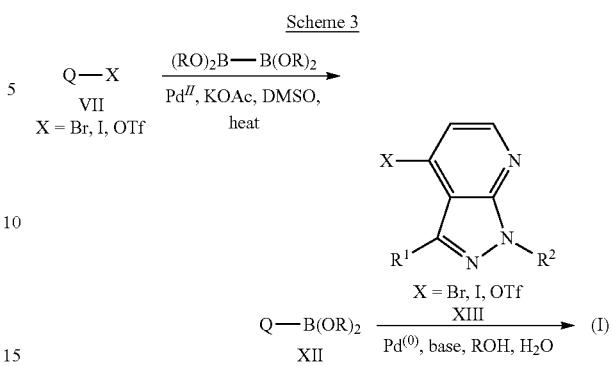

Scheme 4 depicts another method where N-1 of the indazole can be alkylated by treatment of a compound of general structure XIV with an inorganic base, such as cesium carbonate, and a primary or secondary alkyl halide to generate compounds of general structure (I).

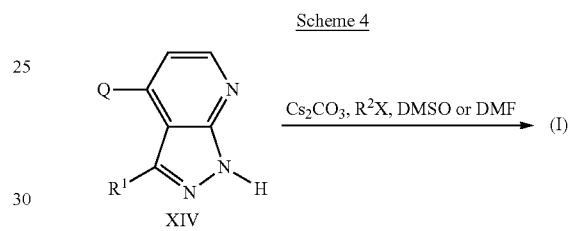

Alternatively, compounds of general structure XIV can be treated with an aryl or heteroaryl bromide, iodide or chloride in the presence of Cu(I), an amine base such as 1,2-cyclohexyldiamine and an inorganic base such as potassium phosphate to afford analogs of general structure (I) as depicted in Scheme 5.

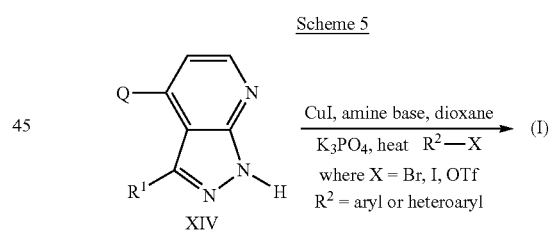

Compounds of structure V can be halogenated at C-3 of the indazole by treatment with, for example NCS as shown in Scheme 6, to give the compound of general structure XIV. This can then be converted to compounds of general structure (I) as described previously.

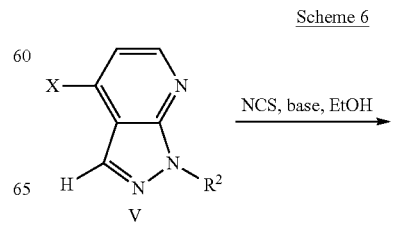

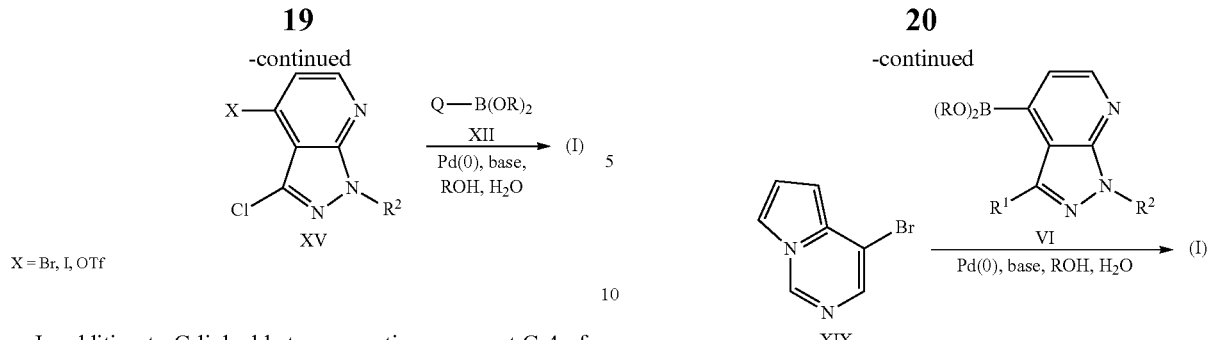

X = Br, I, OTf

In addition to C-linked heteroaromatics groups at C-4 of the indazole core, N-linked analogs can also be made by the method depicted in Scheme 7. Substituted imidazoles XVI, for example, can be coupled with aryl halides of general structure V by treatment with Cu(I) in the presence of an inorganic base and proline to afford compounds of general structure (I).

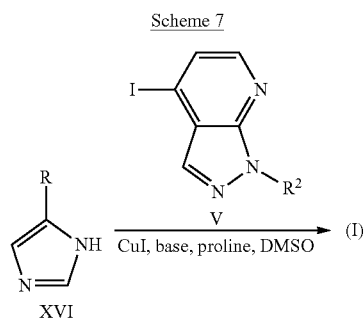

A compound of general structure XVIII can be synthesized from 5-bromopyrimidine by the addition of an alkyllithium reagent to give the corresponding 4-substituted dihydropyrimidine (Scheme 8). Subsequent oxidation by, for example, DDQ then gives the desired 4-substituted pyrimidine. Treatment of this intermediate XVIII with an organic acid, such as formic acid, will generate the corresponding aldehyde. Further reaction of the aldehyde with Burgess reagent will promote cyclization to the pyrrolopyrimidine XIX which can then be converted to a compound of general structure (I) utilizing standard Suzuki conditions as shown previously.

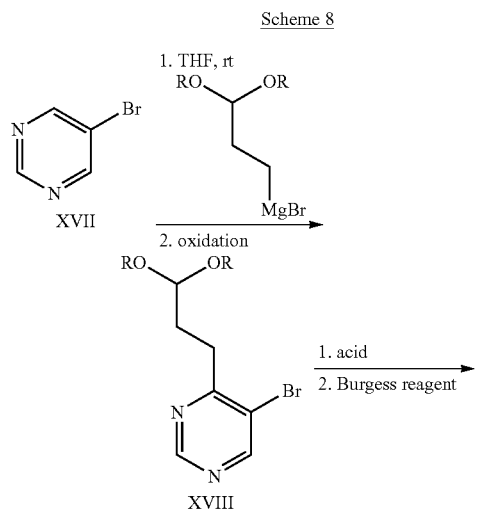

EXAMPLES

The present invention is further defined in the following examples. It should be understood that these examples are given by way of illustration only. From the above discussion and this example, one skilled in the art can ascertain the essential characteristics of this invention, and without departing from the spirit and scope thereof, can make various changes and modifications to the invention to adapt the invention to various uses and conditions. As a result, the present invention is not limited by the illustrative examples set forth herein below, but rather defined by the claims appended hereto.

All temperatures are in degrees Celsius (° C.) unless indicated otherwise herein.

All reactions were carried out with continuous magnetic stirring under an atmosphere of dry nitrogen. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

Abbreviations aq. aqueous
$CH_2Cl_2$ dichloromethane
DDQ 2,3-dichloro-5,6-dicyano-p-benzoquinone
DCE dichloroethane
DCM dichloromethane
DME dimethyl ether
DMSO dimethylsulfoxide
Et ethyl
$Et_2O$ diethyl ether
EtOAc ethyl acetate
EtOH ethanol
g gram(s)
h hour
HCl hydrochloric acid
HPLC high performance liquid chromatography
iPr isopropyl
L liter
LC/MS liquid chromatography/mass spectrometry
LDA lithium diisopropylamine
Me methyl
MeOH methanol
mg milligram(s)
min minute
mL milliliter
mmol millimole(s)
mp melting point
mol moles MS mass spectrometry
NMP N-methylpyrrolidinone
NMR nuclear magnetic resonance
PdCl₂(dppf).CH₂Cl₂ dichloro[1,1'-bis(diphenylphosphino)ferrocene]palladium(II) dichloromethane adduct
Prep HPLC preparative reverse phase HPLC
ret. T HPLC retention time (minutes)
RT or rt room temperature
sat or sat'd saturated
TFA trifluoroacetic acid
THF tetrahydrofuran
TLC thin layer chromatography
μL microliter All final products were characterized by $^1$H NMR, HPLC, electrospray ionization (ESI MS) or atmospheric pressure ionization (API MS) mass spectrometry. $^1$H NMR spectra were obtained on either a 500 MHz JEOL or a 400 MHz Bruker instrument. $^{13}$C NMR spectra were recorded at 100 or 125 MHz. Field strengths are expressed in units of (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

LC/MS Conditions:

Condition A: Waters X-Bridge 4.6×50 mm S10 column, 0% B-100% B with flow rate 4 mL/min and 3 min gradient time; Solvent A: 10% MeOH/90% water/0.1% TFA; Solvent B: 10% water/90% MeOH/0.1% TFA, wavelength 254 nM.

Condition B: PHENOMENEX® Luna 2.0×50 mm 3 μm column, 4 min gradient time, flow rate: 0.8 mL/min; Solvent A: 10% MeOH/90% water/0.1% TFA; Solvent B: 90% MeOH/10% water/0.1% TFA, wavelength 254 nM.

Condition C: Waters Acquity UPLC BEH C18, 2.1×50 mm, 1.7-μm particles; Mobile Phase A: 5:95 acetonitrile:water with 10 mM ammonium acetate; Mobile Phase B: 90:10 acetonitrile:water with 10 mM ammonium acetate; Temperature: 50° C.; Gradient: 0-100% B over 3 minutes, then a 0.75-minute hold at 100% B; Flow: 1.11 mL/min.

Condition D: LC-MS conditions: Column: SUPELCO® Ascentis Express C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 35° C.; Gradient: 0-100% B over 4 minutes, then a 1-minute hold at 100% B; Flow: 4 mL/min.

Condition E: PHENOMENEX® Luna C18 2.5 um 2.0×30 mm, 0% B-100% B with flow rate 4 mL/min and 3 min gradient time; Solvent A: 10% MeOH/90% water/0.1% TFA; Solvent B: 10% water/90% MeOH/0.1% TFA, wavelength 254 nM.

Condition F: Waters Acquity UPLC BEH C18, 2.1×50 mm, 1.7-μm particles; Mobile Phase A: 5:95 acetonitrile:water with 0.05% TFA; Mobile Phase B: 90:10 acetonitrile:water with 0.05% TFA; Temperature: 50° C.; Gradient: 0-100% B over 3 minutes, then a 0.75-minute hold at 100% B; Flow: 1.11 mL/min Preparative HPLC Conditions:

Condition A: Shimadzu preparative HPLC system using a gradient of Solvent A (10% MeOH/90% water/0.1% TFA) and Solvent B (90% MeOH/10% water/0.1% TFA), monitoring at a wavelength of 254 nM, with flow rate=36 mL/min (unless otherwise noted).

Analytical HPLC Conditions:

Condition A: Waters X-Bridge C18, 3.0×150 mm 3.5 M (high pH), 10% B-100% B with flow rate 1 mL/min and gradient time 30 min. Solvent A: 95% water/5% 10 mM ammonium bicarbonate; Solvent B: 95% MeOH/5% water/10 mM ammonium bicarbonate, wavelength 220/254 nM.

Condition B: Waters X-Bridge phenyl, 3.0×150 mm 3.5 M (high pH), 10% B-100% B with flow rate 1 mL/min and gradient time 30 min. Solvent A: 95% water/5% 10 mM ammonium bicarbonate; Solvent B: 95% MeOH/5% water/10 mM ammonium bicarbonate, wavelength 220/254 nM.

Condition C: Waters Sunfire C18, 3.0×150 mm 3.5 μM (low pH), 10% B-100% B with flow rate 1 mL/min and gradient time 30 min. Solvent A: 5% ACN/95% water/0.1% TFA; Solvent B: 95% ACN/5% water/0.1% TFA, wavelength 220/254 nM.

Condition D: Waters X-Bridge phenyl, 3.0×150 mm 3.5 M (low pH), 10% B-100% B with flow rate 1 mL/min and gradient time 30 min. Solvent A: 5% ACN/95% water/0.1% TFA; Solvent B: 95% ACN/5% water/0.1% TFA, wavelength 220/254 nM.

Example 1

4-(1-(4-Fluorophenyl)-1H-pyrazolo[3,4-b]pyridin-4-yl)isoquinoline

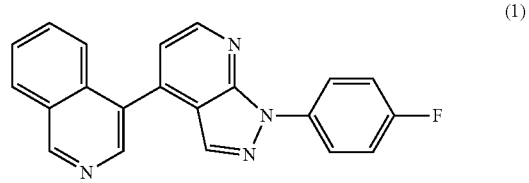 [SMILES: Fc1ccc(-n2ncc3c(-c4cncc5ccccc45)ccnc32)cc1]

(1)

Intermediate 1A 1-(4-Fluorophenyl)-4-iodo-1H-pyrazolo[3,4-b]pyridine

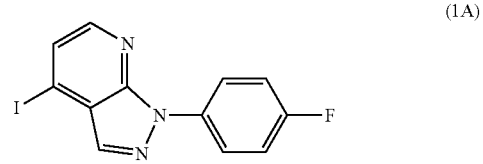 [SMILES: Fc1ccc(-n2ncc3c(I)ccnc32)cc1]

(1A)

To a dry 16×100 mm CHEMGLASS® reaction tube under N₂ was added 2-fluoro-4-iodonicotinaldehyde (600 mg, 2.390 mmol), (4-fluorophenyl)hydrazine (332 mg, 2.63 mmol), and anhydrous NMP (3.2 mL). The reaction mixture was flushed with argon, securely capped, stirred for 20 min at room temperature, and then placed in a 185° C. oil bath for 2 h. The reaction mixture was then allowed to stir at room temperature for 16 h. The reaction mixture was diluted with EtOAc (200 mL) and the organic layer was extracted with water (5×50 mL), brine (1×50 mL), dried over Na₂SO₄, filtered and evaporated to dryness. The residue was purified by BIOTAGE® Silica gel chromatography on a 90 g Thompson Single Step silica cartridge using a linear gradient from 100% hexanes to 100% dichloromethane over 12 column volumes to give 480 mg (59.2%) of the title compound, Intermediate 1A, as an off white solid. $^1$H NMR (500 MHz, CD₃OD) δ ppm 8.22-8.28 (3 H, m), 8.15 (1 H, s), 7.78 (1 H, d, J=4.88 Hz), 7.25-7.37 (2 H, m). LC/MS (Condition A): 100% purity; ret. T=2.9 min, (M+H)+ 339.97.

Example 1

To a dry 16×100 mm CHEMGLASS® reaction tube under N₂ was added 4-(4,4,5,5-tetramethyl-1,3,2-dioxaborolan-2-yl)-isoquinoline (30 mg, 0.118 mmol), Intermediate 1A (39.9 mg, 0.118 mmol), sodium carbonate (56.1 mg, 0.529 mmol), and degassed EtOH:DME:H₂O (1.2:2.5:1.0 ratio) (1.2 mL). The reaction mixture was flushed with argon for 5 min, then treated with tetrakis(triphenylphosphine)palladium(0) (6.79 mg, 5.88 μmol). The reaction mixture was again flushed well with argon, securely capped, and placed in a 105° C. oil bath for 2 h. The reaction mixture was evaporated to dryness, the residue was dissolved in MeOH (5 mL), filtered thru a 45μ frit, and purified by preparative HPLC (Condition A) using a PHENOMENEX® Luna 30×100 mm S10 column from 30% B to 100% B over 12 min., ret. T=10.15 min. The product fractions were applied to a Waters OASIS® MCX 20 cc (1 g) LP extraction cartridge and washed with additional MeOH (50 mL). Elution with Aldrich 2.0M NH₃/MeOH (20 mL) followed by evaporation afforded 21.5 mg (53.2%) of the title compound as a white solid: ¹H NMR (500 MHz, CD₃OD) δ ppm 9.44 (1 H, s), 8.82 (1 H, d, J=4.88 Hz), 8.63 (1 H, s), 8.29-8.36 (3 H, m), 8.00 (1 H, s), 7.80-7.89 (3 H, m), 7.51 (1 H, d, J=4.58 Hz), 7.30-7.39 (2 H, m). LC/MS (Condition B): ret. T=3.415 min, (M+H)+ 341.08. Analytical HPLC: (Condition A): >99%, ret. T=25.35 min, (Condition B): >99%, ret. T=24.37 min, (Condition C): >99%, ret. T=12.63 min, (Condition D): >99%, ret. T=12.13 min.

Example 2

1-(4-Fluorophenyl)-4-(1H-imidazol-1-yl)-1H-pyrazolo[3,4-b]pyridine

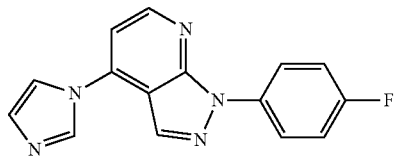

(2)

To a 16×100 mm reaction vial equipped with a magnetic stir bar was added Intermediate 1A (62.8 mg, 0.185 mmol), 1H-imidazole (19.2 mg, 0.282 mmol), potassium carbonate (52.8 mg, 0.382 mmol), D-proline (8.8 mg, 0.076 mmol) and DMSO (1.4 mL). The reaction mixture was degassed with argon for 5 min, then treated with solid copper (I) iodide (7.5 mg, 0.039 mmol). The reaction mixture was again flushed with argon for an additional 5 min, securely capped, and placed in a 95° C. oil bath for 16 h. The reaction mixture was diluted with DMSO (2-3 mL), filtered through a 0.45 uM frit attached to a single-use Waters C-18 SEP-PAK® light cartridge (part #WAT023501) and then purified by preparative HPLC (Condition A) using a Waters Atlantis 30×100 mm S5 column from 20% Solvent B to 85% Solvent B over 12 min, ret. T=7.2 min. The product fractions were poured thru a washed Waters OASIS® MCX 20 cc (1 g) LP extraction cartridge and washed with additional MeOH (50 mL). Elution with Aldrich 2.0M NH₃/MeOH (20 mL) followed by evaporation gives 11.5 mg (22%) of the title compound as a white solid: ¹H NMR (500 MHz, DMSO-d₆) δ ppm 9.41 (1 H, br. s.), 8.82-8.89 (2 H, m), 8.38 (1 H, br. s.), 8.23-8.30 (2 H, m), 7.72-7.83 (2 H, m), 7.43-7.52 (2 H, m). LC/MS (Condition B): ret. T=2.548 min, (M+H)+ 280.06. Analytical HPLC: (Condition A): >97%, ret. T=19.49 min, (Condition B): >98%, ret. T=19.24 min, (Condition C): >98%, ret. T=8.01 min, (Condition D): >98%, ret. T=8.40 min.

Example 3

5-(1-(4-Fluorophenyl)-1H-pyrazolo[3,4-b]pyridin-4-yl)-1,7-naphthyridine

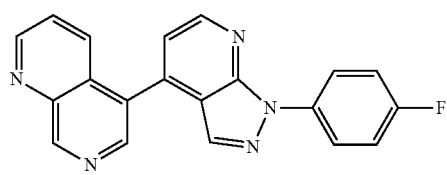

(3)

Intermediate 3A 1-(4-Fluorophenyl)-1H-pyrazolo[3,4-b]pyridin-4-ylboronic Acid

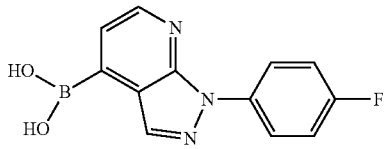

(3A)

To a 16×100 mm reaction vial was added Intermediate 1A (61.8 mg, 0.182 mmol), 4,4,4',4',5,5,5',5'-octamethyl-2,2'-bi(1,3,2-dioxaborolane) (85.5 mg, 0.337 mmol), potassium acetate (77 mg, 0.785 mmol), and DMSO (1 mL). Argon was bubbled into the reaction mixture for 5 minutes. Next, 1,1'-bis(diphenylphosphino)ferrocene-palladium(ii)dichloride dichloromethane complex (10 mg, 0.012 mmol) was added and the reaction mixture was heated at 84° C. for 18 h. The desired product was confirmed to be present by LC/MS (Condition B): 88.0%; ret. T=3.4 min; (M+H)+ 258.04.

Example 3

To Intermediate 3A (23.13 mg, 0.09 mmol) was added 5-bromo-1,7-naphthyridine (59.5 mg, 0.285 mmol), sodium carbonate (56.1 mg, 0.529 mmol), and EtOH:DME:H₂O (1.2:2.5:1.0 ratio) (1.5 mL). The reaction mixture was purged with N₂, then treated with tetrakis(triphenylphosphine)palladium (0). The reaction mixture was purged with argon, securely capped, and placed in a 105° C. oil bath for 3.75 h. The reaction mixture was cooled to room temperature, diluted with DMSO (2-3 mL), filtered through a 0.45 uM frit attached to a single-use Waters C-18 SEP-PAK® light cartridge (part #WAT023501), and then purified by preparative HPLC (Condition A) using a PHENOMENEX® Luna Axia 30×100 mm S10 column from 25% Solvent B to 100% Solvent B over 12 min, ret. T=11.2 min. The product fractions were applied to a washed Waters OASIS® MCX 20 cc (1 g) LP extraction cartridge, washed with additional MeOH (50 mL), and then eluted with Aldrich 2.0M NH$_3$/MeOH (20 mL) to give 9.6 mg (31%) of the title compound as an off white solid following evaporation. $^1$H NMR (500 MHz, DMSO-d$_6$) δ ppm 9.61 (1 H, s), 9.19 (1 H, dd, J=3.97, 1.53 Hz), 8.82-8.91 (2 H, m), 8.31-8.39 (2 H, m), 8.23-8.30 (2 H, m), 7.83 (1 H, dd, J=8.70, 4.12 Hz), 7.60 (1 H, d, J=4.88 Hz), 7.43-7.53 (2 H, m). LC/MS (Condition B): ret. T=3.648 min, (M+H)$^+$ 342.11. Analytical HPLC: (Condition A): >98%, ret. T=21.80 min, (Condition B): >99%, ret. T=21.68 min, (Condition C): >99%, ret. T=15.29 min, (Condition D): >98.9%, ret. T=12.83 min.

Example 4

1-(4-Fluorophenyl)-4-(1-methyl-1H-imidazol-5-yl)-1H-pyrazolo[3,4-b]pyridine (4)

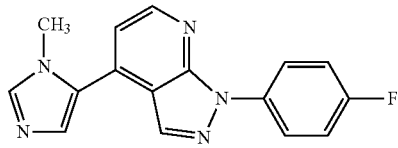

Example 4 was prepared according to the general procedure of Example 1, except that the reaction mixture was heated at 95° C. for 4 h, and using the following materials: Intermediate 1A (38.6 mg, 0.114 mmol), sodium carbonate (54.8 mg, 0.517 mmol), 1-methyl-1H-imidazol-5-ylboronic acid (36.5 mg, 0.290 mmol), EtOH:DME:H$_2$O (1.2:2.5:1.0 ratio) (1.5 mL), and tetrakis(triphenylphosphine)palladium (0) (9.6 mg, 8.31 µmol). The title compound was isolated (3.9 mg (11.45%)) as a white solid. Purification was done by preparative HPLC (Condition A) using a Waters Atlantis 30×100 mm S5 column from 20% Solvent B to 100% Solvent B over 12 min, ret. T=7.16 min. $^1$H NMR (500 MHz, CDCl$_3$) δ ppm 8.60-8.81 (2 H, m), 8.15-8.32 (1 H, m), 8.00-8.12 (2 H, m), 7.58 (1 H, br. s.), 7.11-7.23 (3 H, m), 3.86 (3 H, s). LC/MS (Condition B): ret. T=2.450 min, (M+H)$^+$ 294.10. Analytical HPLC: (Condition A): >97.7%, ret. T=20.24 min, (Condition B): >97.8%, ret. T=20.142 min, (Condition C): >97%, ret. T=9.71 min, (Condition D): >97%, ret. T=10.10 min.

Example 5

3-(4-(1,7-Naphthyridin-5-yl)-1H-pyrazolo[3,4-b]pyridin-1-yl)benzenesulfonamide (5)

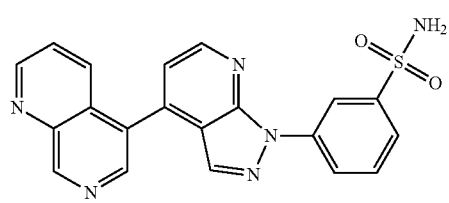

Intermediate 5A 3-(4-Iodo-1H-pyrazolo[3,4-b]pyridin-1-yl)benzenesulfonamide (5A)

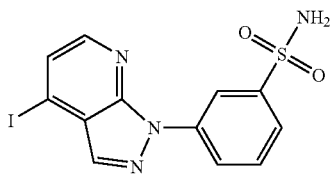

To a 45 mL pressure bottle was added 2-fluoro-4-iodonicotinaldehyde (1.05 g, 4.18 mmol), 3-hydrazinylbenzenesulfonamide (800 mg, 4.27 mmol), and anhydrous NMP (15 mL). The reaction mixture was flushed with argon, securely capped, and heated at 185° C. for 6.5 h. The reaction mixture was cooled to room temperature and slowly added to a rapidly stirred solution of diethyl ether (430 mL). The resulting solid material was filtered and the pale yellow Et$_2$O filtrate was allowed to stand for 18 h at room temperature. The yellow crystals precipitated out and were collected by vacuum filtration to give 425 mg (16.42%) of the title compound as a yellow solid as a "dot" 2 NMP complex by proton NMR. LC/MS (Condition B): ret. T=3.2 min, (M+H)$^+$ 400.83. $^1$H NMR (500 MHz, DMSO-d$_6$) δ 7.56 (s, 2 H) 7.78-7.84 (m, 2 H) 7.89-7.92 (m, 1 H) 8.37-8.42 (m, 2 H) 8.57 (dt, J=4.81, 2.33 Hz, 1 H) 8.75 (s, 1 H). Second and third crops of yellow solid (300 mg, 11.7%; 246 mg, 9.4%) were identical to the first crop of material.

Intermediate 5B 1-(3-Sulfamoylphenyl)-1H-pyrazolo[3,4-b]pyridin-4-ylboronic Acid (5B)

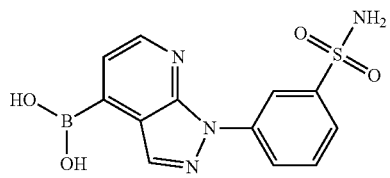

To a 48 mL pressure bottle was added 3-(4-iodo-1H-pyrazolo[3,4-b]pyridin-1-yl)benzenesulfonamide, "dot" 2 1-methyl-2-pyrrolidinone complex (60 mg, 0.100 mmol), 4,4,4',4',5,5,5',5'-octamethyl-2,2'-bi(1,3,2-dioxaborolane) (94.7 mg, 0.373 mmol), potassium acetate (24.4 mg, 0.249 mmol), and anhydrous DMSO (Volume: 2 mL). The reaction mixture was purged well with argon and treated with 1,1'-bis(diphenylphosphino)ferrocenedichloro palladium(II) dichloromethane complex (12.5 mg, 0.017 mmol). The reaction mixture was then heated to 84° C. for 1 h to give the Intermediate 5B. LC/MS (Condition B): ret. T=2.4 min, (M+H)$^+$ 318.98.

Example 5

Example 5 was prepared according to the general procedure of Example 1, except heating at 105° C. for 18 h, and using the following materials: Intermediate 5B (29 mg, 0.091 mmol), 5-bromo-1,7-naphthyridine (40.0 mg, 0.191 mmol), sodium carbonate (44.1 mg, 0.416 mmol), EtOH:DME:H$_2$O (1.2:2.5:1.0 ratio) (1.0 mL), and tetrakis(triphenylphosphine)

palladium(0) (10 mg, 8.6 μmol). The title compound was isolated as a tan solid (7.1 mg, 18.9%). Purification was done by preparative HPLC (Condition A) using a PHENOMENEX® Luna Axia 30×100 mm S10 column from 25% Solvent B to 85% Solvent B over 12 min, ret. T=7.4 min. $^1$H NMR (500 MHz, DMSO-$d_6$) δ ppm 9.62 (1 H, s), 9.10-9.29 (1 H, m), 8.90-8.97 (1 H, m), 8.81-8.88 (2 H, m), 8.63-8.73 (1 H, m), 8.32-8.39 (1 H, m), 8.28 (1 H, d, J=8.55 Hz), 7.79-7.89 (3 H, m), 7.62-7.69 (1 H, m), 7.58 (2 H, s). LC/MS (Condition B): ret. T=2.7 min, (M+H)$^+$ 402.92. Analytical HPLC: (Condition A): >97%, ret. T=15.98 min, (Condition B): >98%, ret. T=18.53 min, (Condition C): >98%, ret. T=11.03 min, (Condition D): >96%, ret. T=10.09 min.

Example 6

3-(4-(1-Methyl-1H-imidazol-5-yl)-1H-pyrazolo[3,4-b]pyridin-1-yl)benzenesulfonamide

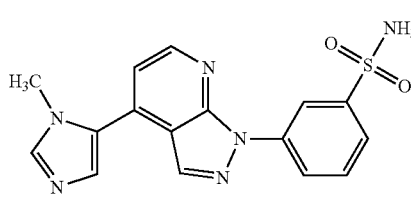

(6)

Example 6 was prepared according to the general procedure of Example 1, except heating at 120° C. for 23 h, and using the following materials: Intermediate 5A (55.9 mg, 0.093 mmol), 1-methyl-1H-imidazol-5-ylboronic acid (43 mg, 0.341 mmol), sodium carbonate (65.3 mg, 0.616 mmol), EtOH:DME:H$_2$O (1.2:2.5:1.0 ratio) (3.0 mL), and tetrakis(triphenylphosphine)palladium(0) (12 mg, 10.38 μmol). The title compound was isolated as a white solid (6.3 mg, 18.9%). Purification was done by preparative HPLC (Condition A) using a PHENOMENEX® Luna Axia 30×100 mm S10 column from 20% Solvent B to 80% Solvent B over 11 min, ret. T=3.72 min. $^1$H NMR (500 MHz, DMSO-$d_6$) δ ppm 3.88 (s, 3 H), 7.54 (s, 1 H), 7.55 (d, J=2.44 Hz, 2 H), 7.68 (s, 1 H), 7.81 (d, J=4.88 Hz, 2 H), 7.99 (s, 1 H), 8.64 (s, 1 H), 8.68 (s, 1 H), 8.77 (d, J=4.88 Hz, 1 H), 8.82 (s, 1 H). LC/MS (Condition B): ret. T=1.8 min, (M+H)$^+$ 355.01. Analytical HPLC: (Condition A): >99%, ret. T=13.37 min, (Condition B): >99%, ret. T=15.65 min, (Condition C): >95%, ret. T=4.66 min, (Condition D): >99%, ret. T=5.06 min.

Example 7

3-(4-(Isoquinolin-4-yl)-1H-pyrazolo[3,4-b]pyridin-1-yl)benzenesulfonamide

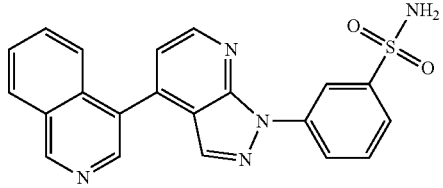

(7)

Example 7 was prepared according to the general procedure in Example 1, except heating at 100° C. for 5.5 h, and using the following materials: Intermediate 5A (57.2 mg, 0.096 mmol), 4-(4,4,5,5-tetramethyl-1,3,2-dioxaborolan-2-yl)isoquinoline (37 mg, 0.145 mmol), sodium carbonate (40 mg, 0.377 mmol), EtOH:DME:H$_2$O (1.2:2.5:1.0 ratio) (3.0 mL), and tetrakis(triphenylphosphine)palladium(0) (12 mg, 10.38 μmol). Example 7 was isolated as a white solid (31.3 mg, 76%). Purification was done by preparative HPLC (Condition A) using a PHENOMENEX® Luna Axia 30×100 mm S10 column from 20% Solvent B to 100% Solvent B over 11 min, ret. T=6.37 min. $^1$H NMR (500 MHz, DMSO-$d_6$) δ ppm 7.57 (s, 2 H), 7.60-7.66 (m, 1 H), 7.84 (d, J=2.44 Hz, 5 H), 8.27-8.29 (m, 1 H), 8.34 (dd, J=5.95, 2.59 Hz, 1 H), 8.67-8.73 (m, 2 H), 8.85 (s, 1 H), 8.89-8.93 (m, 1 H), 9.54 (s, 1 H). LC/MS (Condition B): ret. T=2.51 min, (M+H)$^+$ 402.00. Analytical HPLC: (Condition A): >99%, ret. T=20.03 min, (Condition B): >99%, ret. T=21.92 min, (Condition C): >99%, ret. T=8.21 min, (Condition D): >99%, ret. T=8.29 min.

Example 8

1-(2,4-Difluorophenyl)-4-(pyrrolo[1,2-c]pyrimidin-4-yl)-1H-pyrazolo[3,4-b]pyridine

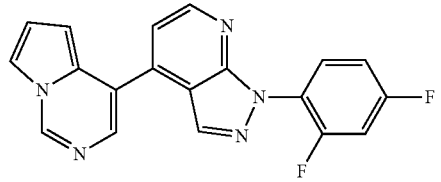

(8)

Intermediate 8A 4-(2-(1,3-Dioxan-2-yl)ethyl)-5-bromopyrimidine

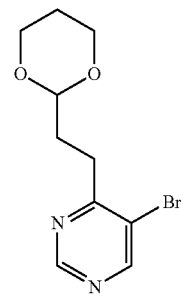

(8A)

To a solution of 5-bromopyrimidine (2 g, 12.58 mmol) in Et$_2$O (40 mL) at room temperature was slowly added (2-(1,3-dioxan-2-yl)ethylmagnesium bromide (0.5M, 27.7 mL, 13.84 mmol). After 1 h, water (2 mL) was added followed by the careful addition of 4,5-dichloro-3,6-dioxocyclohexa-1,4-diene-1,2-dicarbonitrile (3.14 g, 13.84 mmol) as a solution in THF (15 mL). The resulting dark brown suspension was stirred at room temperature for an additional 24 h. The resulting mixture was then diluted with EtOAc and water, the organics were separated and the remaining aqueous layer was extracted twice more. The separated organic layers were combined and washed with 1N NaOH, then washed with brine, dried over sodium sulfate, and concentrated to afford Intermediate 8A (2.62 g, 76% yield). MS (ES): m/z=274.8 [M+H]$^+$. $^1$H NMR (400 MHz, DMSO-d$_6$) δ ppm 9.05 (1 H, s), 8.89 (1 H, s), 4.62 (1 H, t, J=4.95 Hz), 3.92-4.04 (2 H, m), 3.61-3.75 (2 H, m), 2.83-3.00 (2 H, m), 1.77-1.98 (4 H, m).

Intermediate 8B 3-(5-Bromopyrimidin-4-yl)propanal

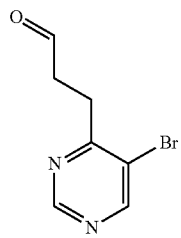

(8B)

To a solution of Intermediate 8A (0.920 g, 3.37 mmol) in DCE (6.5 mL) at 0° C. was slowly added formic acid (6.46 mL, 168 mmol). The system was equipped with a reflux condenser and was heated to 50° C. for 5 h. The resulting solution was allowed to cool to room temperature and the volatile solvents were removed in vacuo. The system was diluted with DCM and washed 1× with saturated aqueous sodium bicarbonate, then washed with brine, dried over sodium sulfate and concentrated to afford Intermediate 8B (724 mg, 100% yield). MS (ES): m/z=216.8 [M+H]. $^1$H NMR (400 MHz, DMSO-d$_6$) δ ppm 9.77 (1 H, s), 9.03 (1 H, s), 8.91 (1 H, s), 3.14 (2 H, t, J=6.60 Hz), 2.96 (3 H, t, J=6.60 Hz).

Intermediate 8C

4-Bromopyrrolo[1,2-c]pyrimidine

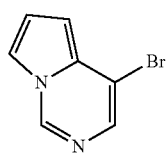

(8C)

To a solution of Intermediate 8B (724 mg, 3.37 mmol) in THF (10 mL) at room temperature was added Burgess Reagent (964 mg, 4.04 mmol). The system was stirred for 10 minutes, at which time it was concluded to be complete. Volatile solvents were removed in vacuo. The crude material was diluted with DCM and washed 1× with water, then washed with brine, dried over sodium sulfate and concentrated to afford Intermediate 8C (664 mg, 100% yield). MS (ES): m/z=198.8 [M+H]$^+$. $^1$H NMR (400 MHz, DMSO-d$_6$) δ ppm 9.17 (1 H, s), 7.81 (1 H, dd, J=2.86, 1.32 Hz), 7.61 (1 H, s), 6.95-7.03 (1 H, m), 6.55 (1 H, d, J=3.96 Hz).

Intermediate 8D 1-(2,4-Difluorophenyl)-4-iodo-1H-pyrazolo[3,4-b]pyridine

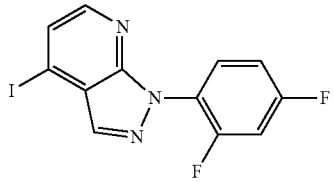

(8D)

To a dry 16×100 mm CHEMGLASS® reaction tube under N$_2$ was added 2-fluoro-4-iodonicotinaldehyde (5 g, 19.92 mmol), (2,4-difluorophenyl)hydrazine (3.01 g, 20.92 mmol) and anhydrous NMP (35 mL). The reaction mixture was flushed with argon, securely capped, stirred for 20 min at room temp, and then placed in a 180° C. oil bath for 4 h. The reaction mixture was then allowed to stir at room temperature for 72 h. The reaction mixture was diluted with EtOAc (1200 mL) and the organic layer was extracted with water (6×350 mL), brine (1×100 mL), dried over Na$_2$SO$_4$, filtered, and evaporated to dryness. The residue was purified by BIOTAGE® Silica gel chromatography on a 300 g Thompson Single Step silica cartridge using a linear gradient from 100% hexanes to 100% dichloromethane over 10 column volumes to give 4.53 g (44.6%) of Intermediate 8D, as a light yellow solid that contained 28% of the uncyclized hydrazone intermediate ((E)-3-((2-(2,4-difluorophenyl)hydrazono)methyl)-2-fluoro-4-iodopyridine). $^1$H NMR (500 MHz, CDCl$_3$) δ 8.21 (1 H, d, J=4.58 Hz), 8.14 (1 H, s), 7.59-7.71 (2 H, m), 7.10 (2 H, td, J=7.55, 3.81 Hz). LC/MS (Condition A): T=3.7 min, (M+H)$^+$ 357.90.

Intermediate 8E 1-(2,4-Difluorophenyl)-1H-pyrazolo[3,4-b]pyridin-4-ylboronic Acid

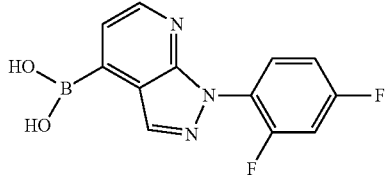

(8E)

Intermediate 8E was prepared according to the general procedure described in Intermediate 3A, except that the reaction mixture was heated at 85° C. for 75 min, using the Intermediate 8D (100 mg, 0.280 mmol), 4,4,4',4',5,5,5',5'-octamethyl-2,2'-bi(1,3,2-dioxaborolane) (133.1 mg, 0.524 mmol), potassium acetate (115.0 mg, 1.172 mmol), and DMSO (1.5 mL). The desired product was confirmed to be present by LC/MS (Condition B): 76%; ret. T=2.9 min; (M+H)$^+$ 276.00.

Example 8

Example 8 was prepared according to the general procedure described for Example 1 using Intermediates 8C and 8E. The crude material was purified by preparative HPLC (Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient 10-100% B over 25 minutes, then a 5-minute hold at 100% B; Flow rate 20 mL/min). The collected fractions were combined and dried by centrifugal evaporation. The material was further purified by preparative LC/MS Waters XBridge C18, 19×250 mm, 5-μm particles column; Mobile Phase A: 5:95 acetonitrile:water with 10-mM ammonium acetate; Mobile Phase B: 95:5 acetonitrile:water with 10-mM ammonium acetate; Gradient: 5-70% B over 25 minutes, then a 10-minute hold at 70% B; Flow: 20 mL/min. The collected fractions were evaporated to yield the title compound (5.4 mg, 15.5%). LC/MS (Condition D): ret time =2.327 min, MS (ES): m/z=347.99 [M+H]$^+$. $^1$H NMR (400 MHz, MeOD) δ ppm 9.04 (1 H, s), 8.65 (1 H, d, J=4.84 Hz), 8.30 (1 H, s), 7.66-7.73 (2 H, m), 7.65 (1 H, s), 7.59 (1 H, d, J=4.84 Hz), 7.55 (1 H, s), 7.10-7.20 (2 H, m), 6.98-7.03 (1 H, m), 6.61 (1 H, d, J=3.74 Hz).

Biological Assays

The pharmacological properties of the compounds of this invention may be confirmed by a number of biological assays. The exemplified biological assays, which follow, have been carried out with compounds of the invention and/or salts thereof.

CYP17 Total SPA Assay

The assays were performed in U-bottom 384-well optiplates. The final assay volume was 15 μl prepared from 7.5 μl additions of microsomes (prepared as a high-speed pellet from homogenized HEK2 cells stably transfected with CYP17), substrates (3H— Pregnenolone and NADPH) and test compounds in assay buffer (50 mM Potassium phosphate pH 7.2, 10% glycerol). The reaction was initiated by the combination of the microsomes and substrates in wells containing compound. The reaction was incubated at room temperature for 45 minutes and terminated by adding 7.5 μl of 0.2N HCl to each well. Following an incubation period of 10 minutes, anti-DHEA-coated SPA beads were added to the terminated reaction. The plate was sealed and incubated overnight with shaking at 4° C. The beads were allowed to settle in the plate for 1 hour and the plate read on a TOPCOUNT® (Perkin-Elmer) plate reader.

Inhibition data were calculated by comparison to no enzyme control reactions for 100% inhibition and vehicle-only reactions for 0% inhibition. The final concentration of reagents in the assays are NADPH, 2 mM; 3H-Pregnenolone, 1 uM; microsomes, 1.25 ug/ml; Anti-DHEA-SPA beads (0.125 mg/well) in 0.5% Triton X-100 and DMSO, 0.05%. Dose response curves were generated to determine the concentration required inhibiting 50% of enzyme activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

Table 1 below lists the $IC_{50}$ values for the following examples of this invention measured in the Total CYP17 SPA Assay hereinabove. The compounds of the present invention, as exemplified by the following examples, showed Human CYP17 SPA $IC_{50}$ values of less than 1 μM.

TABLE 1

Human CYP17 Inhibition

| Example No. | Human CYP17 SPA $IC_{50}$ Value (nM) |
|---|---|
| 1 | 128 |
| 2 | 640 |
| 3 | 41 |
| 4 | 50 |
| 5 | 206 |
| 6 | 271 |
| 7 | 23 |
| 8 | 76 |

CYP17 Lyase Assay

Human CYP17 was expressed in HEK293 cells and microsomal preparations were made and subsequently used as the source of enzyme in the lyase assay. The reaction consists of 200 nM [3H]-Hydroxypregnenolone (ARC), 200 nM 17-Hydroxypregnenolone (Sigma), 2 mM NADPH (CalBiochem), and CYP17-HEK293 microsomes which were incubated in the presence of DMSO or test compounds for 20 minutes at room temperature. Compounds were dissolved in DMSO and serially diluted. The reaction was stopped by the addition of 0.2 N HCl and the product was captured using anti-mouse YSi SPA beads (GE) conjugated to an anti-DHEA monoclonal antibody (Abcam). Signal intensity determined by a Packard Top Count was used to calculate percent inhibition and $IC_{50}$ values.

Cyp17 Hydroxylase Assay

E. coli was transformed to express active human CYP17 and membranes prepared from the transformed E. coli were used as the source of enzyme. The reaction was carried out in a 50 uL final volume containing 200 nM hCYP17 membranes, 25 μM Pregnenolone (Sigma), 7 mM NADPH (CalBiochem), 1 μM cytochrome P450 reductase (Invitrogen), and 50 mM sodium phosphate buffer, pH 7.3. The $IC_{50}$ determination of compounds dissolved in 100% DMSO was done by serial dilution into the assay buffer to a final concentration of 0.2% DMSO. The reaction was incubated at 37° C. for 120 minutes and stopped by the addition of 200 uL of 0.02N HCl in acetonitrile. Samples were then spun at 750000 g and 200 uL of the supernatant was transferred to a clean tube for analysis. The product of the reaction, 17 alpha pregnenolone, was measured via LC/MS.

Cyp17 HEK293 Cell Based Assay

HEK293 cells were stably transfected with human Cyp17 and individual clones analyzed for Cyp17 enzymatic activity via LC/MS. A single clone showing robust activity was selected and scaled up. Cells were seeded in 96 well plates and a serial dilution of compounds dissolved in DMSO was added to the cells. Following an incubation of 4 hours, reactions were neutralized by the addition of 200 ul of acetonitrile containing 0.5 uM pregnenolone as tracer. Plates were spun down at 2K for 15 minutes and supernatants transferred to siliconized 96 well plates. The end product of the reaction DHEA was analyzed via LC/MS.

1-Day Cyno PK/PD Study Protocol

Animals: All procedures involving animals and their care were conducted in conformity with the guidelines that are in compliance with the Bristol-Myers Squibb Institutional Animal Care and Use Committee. Fully mature male cynomolgus monkeys (>4 yrs of age; 5-6 kg) were from an in-house colony. All the monkeys used had chronically implanted femoral vein access ports. For oral studies, all animals were fasted overnight prior to dosing and were fed 4 hr after dosing. All animals had free access to water and were conscious throughout the study.

Drug: For all oral pharmacokinetic studies in cynomolgus monkeys, the tested compound was formulated in polyethylene glycol (PEG 400): water (80:20, v:v) at concentrations of 1-5 mg/mL.

Drug Treatment: The tested compound was administered by oral gavage to cynomolgus monkeys.

Sampling: Blood samples were collected from the femoral port, at 15, 30, and 45 min, and 1, 2, 4, 6, 8, 12, 24, 30, and 48 hr after oral administration. All blood samples were collected into syringes containing sodium heparin. The plasma fraction was immediately separated by centrifugation (14,000 rpm, 10 min, 4° C.), frozen on dry ice, and stored at −20° C. until the samples were analyzed.

Analysis of Tested Compound: Plasma samples were thawed and treated with two volumes of acetonitrile containing internal standard. After centrifugation to remove precipitated proteins, an aliquot of supernatant was analyzed by LC/MS/MS.

Analysis of Steroids. Plasma samples were thawed, and assayed in accordance with package insert instructions for the following kits: Coat-A-Count total testosterone solid phase RIA kit, Coat-A-Count total progesterone solid phase RIA kit, and Coat-A-Count total cortisol solid phase RIA kit (Diagnostic Product Corp, Siemens Healthcare Diagnostics, Deerfield, Ill.).

What is claimed is:

1. A compound of Formula (I):

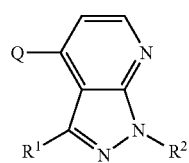

(I)

or pharmaceutically acceptable salts thereof, wherein:

Q is:
(i) 5-membered heteroaryl comprising at least one nitrogen heteroatom and substituted with zero to 2 $R^g$; or
(ii) 9- to 10-membered bicyclic heteroaryl selected from

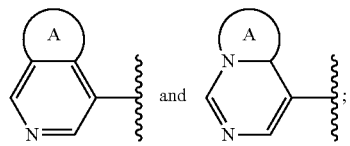

wherein Ring A is a 5- to 6-membered aryl or heteroaryl fused ring substituted with zero to 2 $R^g$;

$R^1$ is:
(i) H, halo, —CN, —$OR^d$, —$NR^eR^e$, or —$C(O)OR^f$;
(ii) $C_{1-6}$alkyl substituted with zero to 4 $R^a$;
(iii) $C_{3-6}$ cycloalkyl substituted with zero to 4 $R^a$;
(iv) aryl substituted with zero to 6 $R^b$;
(v) heterocyclyl substituted with zero to 6 $R^c$; or
(vi) heteroaryl substituted with zero to 6 $R^c$;

$R^2$ is:
(i) $C_{1-6}$alkyl substituted with zero to 4 $R^{a_1}$ where each $R^{a_1}$ is independently halo, —OH, —CN, $C_{3-6}$ cycloalkyl, $C_{1-2}$ fluoroalkyl, $C_{1-6}$ alkoxy, $C_{1-2}$ fluoroalkoxy, —$NR^fR^f$, phenoxy substituted with zero to 4 $R^b$, heterocyclyl substituted with zero to 4 $R^c$, and/or heteroaryl substituted with zero to 4 $R^b$;
(ii) $C_{3-6}$ cycloalkyl substituted with zero to 4 $R^a$;
(iii) —$S(O)_2(C_{1-4}$alkyl), —$S(O)_2(C_{1-4}$fluoroalkyl), or —$C(O)(C_{1-6}$alkyl);
(iv) aryl substituted with zero to 6 $R^b$;
(v) heterocyclyl substituted with zero to 6 $R^c$; or
(vi) heteroaryl substituted with zero to 6 $R^c$;

each $R^a$ is independently halo, —OH, —CN, $C_{3-6}$cycloalkyl, $C_{1-2}$fluoroalkyl, $C_{1-6}$alkoxy, $C_{1-2}$fluoroalkoxy, —$NR^fR^f$, phenyl substituted with zero to 5 $R^b$, phenoxy substituted with zero to 4 $R^b$, heterocyclyl substituted with zero to 4 $R^c$, and/or heteroaryl substituted with zero to 4 $R^b$;

each $R^b$ is independently halo, —OH, —CN, $C_{1-4}$alkyl, $C_{3-6}$cycloalkyl, $C_{1-2}$fluoroalkyl, $C_{1-6}$alkoxy, $C_{1-4}$fluoroalkoxy, —$NR^fR^f$, —$C(O)OH$, —$S(O)_2(C_{1-4}$alkyl), —$S(O)_2NR^fR^f$, and/or heterocyclyl substituted with zero to 4 $R^c$;

each $R^c$ is independently halo, —CN, —OH, $C_{1-4}$alkyl, $C_{3-6}$cycloalkyl, $C_{1-2}$fluoroalkyl, $C_{1-6}$alkoxy, $C_{1-4}$fluoroalkoxy, —$NR^fR^f$, azetidine, and/or pyrrolidine, or two $R^c$ attached to the same atom can form =O;

each $R^d$ is:
(i) $C_{1-4}$alkyl substituted with zero to 4 $R^a$;
(ii) $C_{3-6}$ cycloalkyl substituted with zero to 4 $R^a$;
(iii) aryl substituted with zero to 6 $R^b$;
(iv) heterocyclyl substituted with zero to 6 $R^c$; and/or
(v) heteroaryl substituted with zero to 6 $R^c$;

each $R^e$ is independently:
(i) H;
(ii) $C_{1-4}$alkyl substituted with zero to 4 $R^a$; and/or
(iii) $C_{3-6}$ cycloalkyl substituted with zero to 4 $R^a$;
or two $R^e$ attached to the same nitrogen atom can form a 5-6 membered heterocyclyl ring having one additional heteroatom, and substituted with zero to 2 substituents independently selected from —CN, —OH, and/or $C_{1-4}$alkyl;

each $R^f$ is independently H, $C_{1-6}$alkyl, $C_{3-6}$cycloalkyl, $C_{1-4}$fluoroalkyl, and/or aryl; and each $R^g$ is independently:
(i) halo, —CN, —$OR^d$, —$NR^eR^e$, or —$C(O)OR^f$;
(ii) $C_{1-6}$alkyl substituted with zero to 4 $R^a$;
(iii) $C_{3-6}$ cycloalkyl substituted with zero to 4 $R^a$;
(iv) aryl substituted with zero to 6 $R^b$;
(v) heterocyclyl substituted with zero to 6 $R^c$; or
(vi) heteroaryl substituted with zero to 6 $R^c$.

2. The compound according to claim 1 or pharmaceutically acceptable salts thereof, wherein Q is an imidazolyl substituted with zero to 2 $R^g$.

3. The compound according to claim 2 or pharmaceutically acceptable salts thereof, wherein Q is:

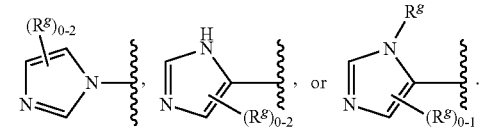

4. The compound according to claim 1 or pharmaceutically acceptable salts thereof, wherein Q is a 9- to 10-membered bicyclic heteroaryl selected from

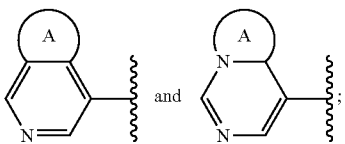

wherein Ring A is a 5- to 6-membered aryl or heteroaryl fused ring substituted with zero to 2 $R^g$.

5. The compound according to claim 4 or pharmaceutically acceptable salts thereof, wherein Q is:

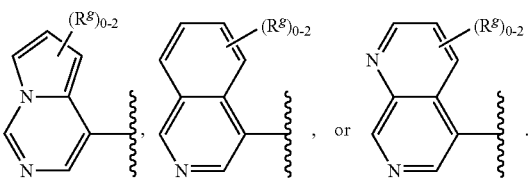

6. The compound according to claim 1 or pharmaceutically acceptable salts thereof, wherein Q is

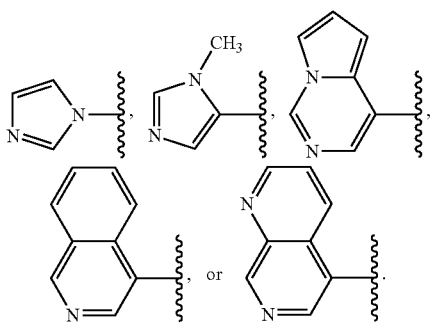

7. The compound according to claim 1 or pharmaceutically acceptable salt thereof, wherein said compound is selected from 4-(1-(4-fluorophenyl)-1H-pyrazolo[3,4-b]pyridin-4-yl)isoquinoline (1); 1-(4-fluorophenyl)-4-(1H-imidazol-1-yl)-1H-pyrazolo[3,4-b]pyridine (2); 5-(1-(4-fluorophenyl)-1H-pyrazolo[3,4-b]pyridin-4-yl)-1,7-naphthyridine (3); 1-(4-fluorophenyl)-4-(1-methyl-1H-imidazol-5-yl)-1H-pyrazolo[3,4-b]pyridine (4); 3-(4-(1,7-naphthyridin-5-yl)-1H-pyrazolo[3,4-b]pyridin-1-yl)benzenesulfonamide (5); 3-(4-(1-methyl-1H-imidazol-5-yl)-1H-pyrazolo[3,4-b]pyridin-1-yl)benzenesulfonamide (6); 3-(4-(isoquinolin-4-yl)-1H-pyrazolo[3,4-b]pyridin-1-yl)benzenesulfonamide (7); and 1-(2,4-difluorophenyl)-4-(pyrrolo[1,2-c]pyrimidin-4-yl)-1H-pyrazolo[3,4-b]pyridine (8).

8. A pharmaceutical composition, comprising a pharmaceutically acceptable carrier and a compound according to claim 1 or pharmaceutically acceptable salts thereof.

9. The compound according to claim 1 or pharmaceutically acceptable salts thereof, wherein Q is pyrrolyl, imidazolyl, isoxazolyl, oxazolyl, isothiazolyl, triazolyl or oxadiazolyl, each of which is substituted with zero to 2 $R^g$.

10. The compound according to claim 6 or pharmaceutically acceptable salts thereof, wherein:
$R^1$ is H; and
$R^2$ is fluorophenyl, difluorophenyl, or phenyl substituted with —$SO_2NH_2$.

11. The compound according to claim 4 or pharmaceutically acceptable salts thereof, wherein Q is pyrrolo[1,2-c]pyrimidinyl, isoquinolinyl, 4aH-pyrido[1,2-c]pyrimidinyl, 1,6-naphthyridinyl, or 1,7-naphthyridinyl.

12. The compound according to claim 1, wherein $R^1$ is:
(i) H, F, Cl, —CN, —OH, —$OCH_3$, —$NH_2$, —$NHCH_3$, —$N(CH_3)_2$, —COOH, or —$COOCH_3$;
(ii) $C_{1-6}$ alkyl substituted with zero to 4 $R^a$, in which $R^a$ is independently —$CH_2F$, —$CF_3$, and/or $C_{3-6}$ cycloalkyl;
(iii) $C_3$-$C_6$ cycloalkyl substituted with zero to 4 $R^a$;
(iv) phenyl substituted with zero to 3 $R^b$ groups, where $R^b$ is independently selected from F, Cl, —CN, —$CH_3$, —$CF_3$, —$OCH_3$, —$OCF_3$, —$NH_2$, and/or —$SO_2NH_2$;
(v) azetidinyl, tetrahydrofuranyl, pyrrolidinyl, tetrahydropyranyl, piperidinyl, morpholinyl, or piperazinyl, each of which is substituted with zero to 6 $R^c$; or
(vi) pyrrolyl, furanyl, pyrazolyl, imidazolyl, isoxazolyl, oxazolyl, thiazolyl, triazolyl, oxadiazolyl, pyridinyl, pyridazinyl, pyrimidinyl, or pyrazinyl, each of which is substituted with zero to 3 $R^c$.

13. The compound according to claim 1 or pharmaceutically acceptable salts thereof wherein $R^2$ is:
(i) $C_{1-4}$ alkyl substituted with zero to 4 $R^{a1}$;
(ii) $C_{3-6}$ cycloalkyl substituted with zero to 4 $R^a$;
(iii) —$S(O)_2(C_{1-2}$ alkyl), —$S(O)_2(C_{1-2}$ fluoroalkyl), or $C(O)(C_{1-3}$ alkyl);
(iv) phenyl substituted with zero to 4 $R^b$ independently selected from F, Cl, —CN, —OH, —$CH_3$, —$CF_3$, —$OCH_3$, —$OCF_3$, —$NH_2$, and/or —$SO_2NH_2$;
(v) azetidinyl, tetrahydrofuranyl, pyrrolidinyl, tetrahydropyranyl, piperidinyl, morpholinyl, or piperazinyl, each of which is substituted with zero to 6 $R^c$; or
(vi) pyrrolyl, furanyl, pyrazolyl, imidazolyl, isoxazolyl, oxazolyl, thiazolyl, triazolyl, oxadiazolyl, pyridinyl, pyridazinyl, pyrimidinyl, or pyrazinyl, each of which is substituted with zero to 3 $R^c$.

* * * * *